(12) United States Patent
McConnachie et al.

(10) Patent No.: US 6,569,820 B2
(45) Date of Patent: May 27, 2003

(54) MANUFACTURE OF LUBRICANT ADDITIVES

(75) Inventors: Jonathan M. McConnachie, Flemington, NJ (US); Ian A. W. Bell, Southmoor Oxford (GB); Edward I. Stiefel, Bridgewater, NJ (US); Stanley J. Brois, Westfield, NJ (US); Ernestine W. Hill, Piscataway, NJ (US); Alisdair J. Brown, Chilton Didcot (GB)

(73) Assignee: Infineum International Ltd. (GB)

( * ) Notice: Subject to any disclaimer, the term of this patent is extended or adjusted under 35 U.S.C. 154(b) by 165 days.

(21) Appl. No.: 09/816,053

(22) Filed: Mar. 23, 2001

(65) Prior Publication Data

US 2001/0053751 A1 Dec. 20, 2001

(30) Foreign Application Priority Data

Mar. 29, 2000 (EP) ............................................. 00201136

(51) Int. Cl.⁷ ........................ C10M 139/00; C07F 11/00
(52) U.S. Cl. ............................ 508/363; 556/38; 556/57
(58) Field of Search ......................................... 508/363

(56) References Cited

U.S. PATENT DOCUMENTS

| | | | | | |
|---|---|---|---|---|---|
| 5,631,213 A | * | 5/1997 | Tanaka et al. | ............... | 508/363 |
| 5,688,748 A | * | 11/1997 | Tomizawa | ................... | 508/363 |
| 5,824,627 A | * | 10/1998 | McConnachie et al. | ..... | 508/363 |
| 5,837,657 A | * | 11/1998 | Fang et al. | .................. | 508/363 |
| 5,888,945 A | * | 3/1999 | Stiefel et al. | ............... | 508/363 |
| 5,895,779 A | * | 4/1999 | Boffa | .......................... | 508/555 |
| 5,906,968 A | * | 5/1999 | McConnachie et al. | ..... | 508/363 |
| 6,010,987 A | * | 1/2000 | Stiefel et al. | ............... | 508/363 |
| 6,110,878 A | * | 8/2000 | McConnachie et al. | ..... | 508/363 |
| 6,211,123 B1 | * | 4/2001 | Brown et al. | ............... | 508/363 |
| 6,232,276 B1 | * | 5/2001 | Stiefel et al. | ............... | 508/363 |
| 6,358,894 B1 | * | 3/2002 | Leta et al. | ................... | 508/363 |

FOREIGN PATENT DOCUMENTS

| WO | WO98/26030 | 6/1998 | ........ C10M/159/18 |
|---|---|---|---|
| WO | WO99/33113 | 6/1999 | ............ C07F/11/00 |

OTHER PUBLICATIONS

Chemical Abstracts, vol. 114, No. 12, Mar. 25, 1991, Columbus, OH, Abstract No. 113948 Hegetschweiler et al., Identification and Characterization of Trinuclear Molybdenum–Sulfur Clusters by Fast Atom Bombardment (FAB) Mass Spectroscopy, XP002144193.

Inorganic Chemistry, vol. 30, No. 4, 1991, pp. 873–876.

* cited by examiner

*Primary Examiner*—Ellen M. McAvoy

(57) ABSTRACT

Oil-soluble or oil-dispersible trinuclear molybdenum-sulfur compounds are made by reacting, in a polar medium, a reactant molybdenum compound containing an anion that possesses a trinuclear molybdenum core, and a dithiocarbamate that is produced in situ.

9 Claims, No Drawings

MANUFACTURE OF LUBRICANT ADDITIVES

This invention relates to a method of making oil-soluble or oil-dispersible trinuclear molybdenum compounds that may be useful as additives in lubricating oil compositions (or lubricants).

EP-A-0 960 178, based on International Patent Application PCT/IB 97 016 56, describes trinuclear molybdenum compounds as lubricant additives, such as for providing antifriction, antiwear and/or antioxidant properties. It also describes methods of making such compounds, in a form comprising a trinuclear molybdenum core having ligands bonded thereto capable of rendering the compounds oil-soluble or oil-dispersible. However, these methods involve pre-preparation of a ligand source reactant, ie additional process steps to prepare starting materials are required thereby raising manufacturing costs. Also, the reactions may not always be controllable or "tailorable".

It has now been found that the trinuclear compounds can be made by reaction of a molybdenum compound with a ligand source reactant prepared in situ thereby alleviating the above problem.

Thus, in one aspect, the invention is a method of making an oil-soluble or oil-dispersible trinuclear molybdenum-sulfur compound comprising a trinuclear molybdenum core bonded to one or more dithiocarbamate ligands capable of rendering the compound oil-soluble or oil-dispersible, which method comprises reacting in a polar medium (A) a reactant molybdenum compound containing an anion that possesses a trinuclear molybdenum core, such as a thio- or polythio-trinuclear molybdenum core, and (B) a dithiocarbamate that it produced in situ.

The reactant molybdenum compound need not be derivatised, eg it need not be in the form of a halide derivative such as described in the art.

The invention is surprising in view of statements in the art, such as by Zimmermann et al in Inorganic Chemistry, Vol 30, No 23, 1991, 4336–4341, that redox potential of an oxidising agent may be necessary for the success of analogous reactions.

In a second aspect, the invention is a lubricating oil composition comprising a major amount of an oil of lubricating viscosity and a minor amount of a trinuclear molybdenum-sulfur compound made by the method of the first aspect.

In a third aspect, the invention is a method of making a lubricating oil composition comprising blending a major amount of an oil of lubricating viscosity and a minor amount of a trinuclear molybdenum-sulfur compound made by the method of the first aspect.

In a fourth aspect, the invention is a method of lubricating an internal combustion engine comprising supplying to the engine a lubricating oil composition of the second aspect or made by the method of the third aspect.

In a fifth aspect, the invention is a method for reducing one or more of the friction, wear and oxidancy, and retention of these properties, of an internal combustion engine comprising treating moving surfaces thereof with a lubricating oil composition of the second aspect or made by the method of the third aspect.

In a sixth aspect, the invention is a method for reducing the fuel consumption of an internal combustion engine, and retention of the property, comprising treating moving surfaces thereof with a lubricating oil composition of the second aspect or made by the method of the third aspect.

The features of the invention will now be discussed in more detail.

The compounds made by the present invention have, as stated above, a trinuclear molybdenum-sulfur core to which the dithiocarbamate ligands are bonded. They may, for example, have the formula $Mo_3S_xdtc_y$ wherein x is from 4 to 10, such as 4 to 7, preferably 4 or 7;

dtc represents the dithiocarbamate; and y is a number to neutralise the charge on the $Mo_3S_x$ core.

By "bonded" in this specification is meant to include covalent bonding, bonding by electrostatic interaction as in the case of a counter-ion, and forms of bonding intermediate between covalent and electrostatic bonding. Dtc ligands within the same compound may be differently bonded. For example, when y is 4, three of dtc may be covalently bonded and the fourth of dtc electrostatically bonded.

An example of reactant compound (A) is one that contains the $[Mo_3S_{13}]^{2-}$ ion, for example an ammonium salt thereof such as $(NH_4)_2Mo_3S_{13} \cdot nH_2O$, wherein n is 0 to 2, including non-integer values.

The dithiocarbamate, (B), may be a hydrocarbyl-substituted dithiocarbamate, preferably dihydrocarbyl-substituted.

The term "hydrocarbyl" denotes a substituent having a carbon atom directly attached to the remainder of the ligand and is predominantly hydrocarbyl in character within the context of this invention. Such substituents include the following: (1) hydrocarbon substituents, that is, aliphatic (for example alkyl or alkenyl), alicyclic (for example cycloalkyl or cycloalkenyl) substituents, aromatic-, aliphatic- and alicyclic-substituted aromatic nuclei, as well as cyclic substituents wherein the ring is completed through another portion or the residue (that is, any two indicated substituents may together form an alicyclic group); (2) substituted hydrocarbon substituents, that is, those containing non-hydrocarbon groups which, in the context of this invention, do not alter the predominantly hydrocarbyl character of the substituent. Those skilled in the art will be aware of suitable groups (e.g., halo, (especially chloro and fluoro), amino, alkoxyl, mercapto, alkylmercapto, nitro, nitroso and sulfoxy); (3) hetero substituents, that is, substituents which, while predominantly hydrocarbon in character within the context of this invention, contain atoms other than carbon present in a chain or ring otherwise composed of carbon atoms.

The hydrocarbyl groups are preferably alkyl (e.g., in which the carbon atom attached to the remainder of the ligand is primary, secondary or tertiary), aryl, substituted aryl and ether groups.

Importantly, the hydrocarbyl groups have a sufficient number of carbon atoms to render the compounds soluble or dispersible in oil. The compounds' oil solubility or dispersibility may be influenced by the number of carbon atoms in the ligands. Preferably the ligands have a sufficient number of carbon atoms to render the compound soluble or dispersible in oil. The total number of carbon atoms present among all of the hydrocarbyl groups of the compounds' ligands typically will be at least 21, e.g., 21 to 800, such as at least 25, at least 30 or at least 35. For example, the number of carbon atoms in each alkyl group will generally range between 1 to 100, preferably 1 to 40, and more preferably between 3 and 20.

The dithiocarbamate may be prepared in situ, for example by providing carbon disulfide and a hydrocarbyl-substituted amine such as a secondary alkylamine under conditions to react to produce the dithiocarbamate, (B), which, in turn, reacts with reactant (A).

The polar medium (or solvent) may, for example be toluene, tetrahydrofuran (THF), dimethylformamide (DMF), methanol, or water. Also, base, such as an alkali metal hydroxide, eg NaOH, may be provided.

The resulting product, such as $Mo_3S_xL_y$, in the reaction mixture may be isolated. Any excess of the reactant compound containing the anion resulting from the method of the present invention may, if desired, be removed such as by filtration.

The reaction product may be useful as a multifunctional lubricating oil additive having enhanced antifriction, antiwear and antioxidant properties and may be used to enhance antifriction, antiwear and antioxidancy properties of an oil of lubricating viscosity by adding the reaction product thereto to produce a lubricating oil composition.

Other additives such as known in the art may be incorporated, provided they are different from those of the invention. Examples are dispersants, detergents, rust inhibitors, anti-wear agents, anti-oxidants, corrosion inhibitors, friction modifiers, pour point depressants, anti-foaming agents, viscosity modifiers and surfactants.

In the preparation of lubricating oil compositions, it is common practice to introduce additive(s) therefor in the form of concentrates of the additive(s) in a suitable oleaginous, typically hydrocarbon, carrier fluid, e.g. mineral lubricating oil, or other suitable solvent. Oils of lubricating viscosity as well as aliphatic, naphthenic, and aromatic hydrocarbons are examples of suitable carrier fluids for concentrates.

Concentrates constitute a convenient means of handling additives before their use, as well as facilitating solution or dispersion of additive in lubricating oil compositions. When preparing a lubricating oil composition that contains more than one type of additive (sometimes referred to as "additive components"), each additive may be incorporated separately—each in the form of a concentrate. In may instances, however, it is convenient to provide a so-called additive "package" (also referred to as an "adpack") comprising two or more additives in a single concentrate.

A concentrate may contain 1 to 90, such as 10 to 80, preferably 20 to 80, more preferably 20 to 70, mass % active ingredient of the additive or additives.

Lubricating oil compositions may be prepared by adding to an oil of lubricating viscosity a mixture of an effective minor amount of at least one additive and, if necessary, one or more co-additives such as described herein. The preparation may be accomplished by adding the additive directly to the oil or by adding it in the form of a concentrate thereof to disperse or dissolve the additive. Additives may be added to the oil by any method known to those skilled in the art, either prior to, contemporaneously with, or subsequent to addition of other additives.

EXAMPLES

The invention may be demonstrated with reference to the following examples.

As used herein "coco" is an alkyl chain or mixture of alkyl chains of varying even numbers of carbon atoms, typically from $C_6$ to $C_{18}$.

General Procedure A

Synthesis of $Mo_3S_7dtc_4$ was carried out by combining $(NH_4)_2Mo_3S_{13} \cdot 2H_2O$ (referred to as ATM), dioctyl amine, and optionally sodium hydroxide, with a solvent under a nitrogen atmosphere followed by addition of carbon disulfide and stirring for two hours to complete the formation of a dithiocarbamate. The mixture was then heated to an appropriate temperature for approximately 16 hours (under reflux, except when the solvent was dimethylformamide). The solvent, unless it was toluene, was removed from the product, which was then dissolved in toluene and filtered to remove any solid by-products. The toluene was then removed to give the final product.

GENERAL PROCEDURE A:-

| Example | Molar Ratio (ATM: octyl$_2$NH: CS$_2$:NaOH) | Solvent | Temperature (° C.) |
|---|---|---|---|
| 1 | 1 : 10 : 10 : 0 | MeOH | 65 |
| 2 | 1 : 10 : 10 : 0 | MeOH | 65 |
| 3 | 1 : 10 : 10 : 0 | DMF | 110 |
| 4 | 1 : 10 : 10 : 0 | THF | 67 |
| 5 | 1 : 4 : 4 : 0 | MeOH | 65 |
| 6 | 1 : 4 : 4 : 0 | toluene | 110 |
| 7 | 1 : 4 : 4 : 0 | THF | 67 |
| 8 | 1 : 4 : 4 : 0 | DMF | 110 |

DMF = dimethylformamide
THF = tetrahydrofuran

General Procedure B

Synthesis of $Mo_3S_7dtc_4$ was carried out by combining dioctyl amine, optionally sodium hydroxide, and carbon disulfide with a solvent under a nitrogen atmosphere and stirred for two hours followed by addition of ATM. The mixture was then heated to an appropriate temperature for approximately 16 hours (under reflux, except when the solvent was water).

The product was treated as described in GENERAL PROCEDURE A. The following specific examples were carried out using GENERAL PROCEDURE B.

| Example | Molar Ratio (ATM: octyl$_2$NH: CS$_2$:NaOH) | Solvent | Temperature (° C.) |
|---|---|---|---|
| 9 | 1 : 4 : 4 : 0 | MeOH | 65 |
| 10 | 1 : 4 : 4 : 0 | toluene | 110 |
| 11 | 1 : 4 : 4 : 0 | water | 65 |
| 12 | 1 : 4 : 4 : 4 | water | 65 |

General Procedure C

Synthesis of $Mo_3S_7dtc_4$ was carried out by adding ATM and dicocoamine to MeOH, as solvent, under a nitrogen atmosphere, followed by addition of carbon disulfide and stirring for two hours to complete formation of a dithiocarbamate. The mixture was heated to 65° C. for eight hours, MeOH removed, and the product mixed with a mineral oil (ESN 150). The final product was analysed quantitatively for Mo and S.

The following specific examples were carried out using GENERAL PROCEDURE C.

| Example | Molar Ratio (ATM: coco$_2$NH:CS$_2$) | Mo (mass %) | S (mass %) |
|---|---|---|---|
| 13 | 1 : 4 : 4 | 7.89 | 13.5 |
| 14 | 1 : 4 : 10 | 8.22 | 13.78 |

-continued

| Example | Molar Ratio (ATM: coco$_2$NH:CS$_2$) | Mo (mass %) | S (mass %) |
|---|---|---|---|
| 15 | 1 : 10 : 10 | 5.23 | 10.73 |
| 16 | 1 : 10 : 4 | 4.17 | 7.54 |

The products of all of the above examples were found to exhibit satisfactory properties as lubricant additives.

What is claimed is:

1. A method of making an oil-soluble or oil-dispersible trinuclear molybdenum-sulfur compound comprising a trinuclear molybdenum core bonded to one or more dithiocarbamate ligands capable of rendering the compound oil-soluble or oil-dispersible, which method comprises reacting in a polar medium
   (A) a reactant molybdenum compound containing an anion that possesses a trinuclear molybdenum core and
   (B) a dithiocarbamate that is produced in situ.

2. The method as claimed in claim 1 wherein the reactant molybdenum compound contains the $[Mo_3S_{13}]^{2-}$ ion.

3. The method as claimed in claim 1 wherein the dithiocarbamate is produced in situ by providing carbon disulfide and a secondary amine under conditions suitable to cause the carbon disulfide and secondary amine to react to produce the dithiocarbamate.

4. The method as claimed in claim 1 wherein the polar medium is toluene, tetrahydrofuran, dimethylformamide, methanol, or water.

5. The method as claimed in claim 1 wherein the trinuclear molybdenum compound has the formula $Mo_3S_xL_y$
   wherein x is from 4 to 10
   L represents the dithiocarbamate ligands, and
   y is a number to neutralise the charge on the $Mo_3S_x$ core.

6. The method as claimed in claim 1 wherein the dithiocarbamate is a hydrocarbyl-substituted dithiocarbamate.

7. The method as claimed in claim 6 wherein the hydrocarbyl groups are alkyl groups.

8. The method as claimed in claim 7 wherein the alkyl groups have from 3 to 20 carbon atoms.

9. The method of claim 1, wherein said trinuclear molybdenum core is selected from the group consisting of thio- and polythio-trinuclear molybdenum cores.

* * * * *